US010213290B2

(12) United States Patent
Hingston et al.

(10) Patent No.: US 10,213,290 B2
(45) Date of Patent: Feb. 26, 2019

(54) BRAIDED STENT AND METHOD OF MANUFACTURING A BRAIDED STENT

(71) Applicant: BOSTON SCIENTIFIC SCIMED, INC., Maple Grove, MN (US)

(72) Inventors: John A. Hingston, Framingham, MA (US); Brian Gaffney, Rutland, MA (US); Colby Harris, Weston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/434,182

(22) Filed: Feb. 16, 2017

(65) Prior Publication Data
US 2017/0231746 A1 Aug. 17, 2017

Related U.S. Application Data

(60) Provisional application No. 62/296,503, filed on Feb. 17, 2016.

(51) Int. Cl.
*A61F 2/90* (2013.01)
*A61F 2/04* (2013.01)

(52) U.S. Cl.
CPC .......... *A61F 2/04* (2013.01); *A61F 2/90* (2013.01); *A61F 2220/0058* (2013.01); *A61F 2230/0034* (2013.01); *A61F 2230/0069* (2013.01); *A61F 2240/001* (2013.01); *A61F 2250/001* (2013.01)

(58) Field of Classification Search
CPC ........................................................ A61F 2/90
See application file for complete search history.

(56) References Cited

U.S. PATENT DOCUMENTS

| | | |
|---|---|---|
| 5,304,200 A | 4/1994 | Spaulding |
| 6,027,529 A | 2/2000 | Roychowdhury et al. |
| 6,083,257 A | 7/2000 | Taylor et al. |
| 6,136,023 A | 10/2000 | Boyle |
| 6,295,714 B1 | 10/2001 | Roychowdhury et al. |
| 6,494,907 B1 | 12/2002 | Bulver |
| 6,547,819 B2 | 4/2003 | Strecker |
| 7,311,031 B2 | 12/2007 | McCullagh et al. |
| 7,695,506 B2 | 4/2010 | Thistle et al. |
| 7,993,387 B2 | 8/2011 | Clerc et al. |
| 8,636,790 B2 | 1/2014 | Igaki |
| 8,677,874 B2 | 3/2014 | Lilburn et al. |
| 8,771,337 B2 | 7/2014 | Williams et al. |
| 9,155,643 B2 | 10/2015 | Clerc et al. |
| 2004/0024416 A1* | 2/2004 | Yodfat ............... A61F 2/01 606/200 |
| 2007/0112415 A1 | 5/2007 | Bartlett |
| 2011/0224707 A1* | 9/2011 | Miloslavski ........ A61B 17/221 606/159 |
| 2011/0265908 A1 | 11/2011 | Clerc et al. |
| 2011/0295359 A1 | 12/2011 | Clerc et al. |
| 2013/0018318 A1 | 1/2013 | Ravichandran et al. |

(Continued)

*Primary Examiner* — Jeffry H Aftergut
(74) *Attorney, Agent, or Firm* — Seager, Tufte & Wickhem, LLP

(57) ABSTRACT

A stent may be actuatable between a delivery configuration and a deployed configuration. A stent may include one or more interwoven filaments each including a cross-sectional profile having at least one flattened portion. A flattened portion of a first filament portion of the one or more filaments may be positioned in contact with a flattened portion of a second filament portion of the one or more filaments.

19 Claims, 9 Drawing Sheets

(56) References Cited

U.S. PATENT DOCUMENTS

2013/0184833 A1 7/2013 Ryan et al.
2014/0074220 A1 3/2014 Clerc et al.
2014/0277339 A1 9/2014 Thompson

* cited by examiner

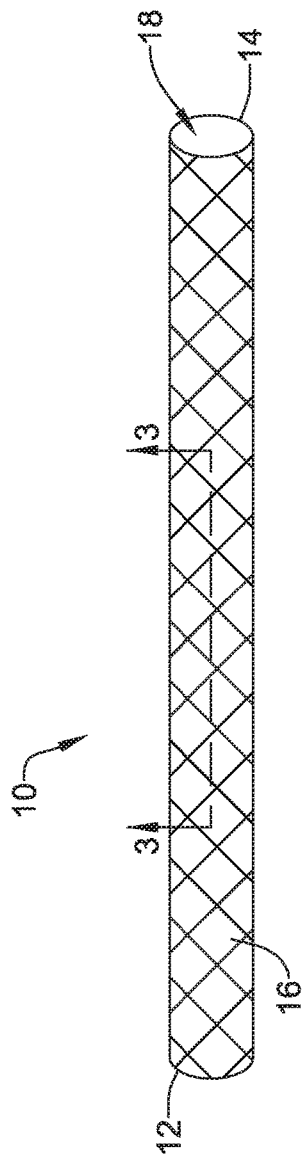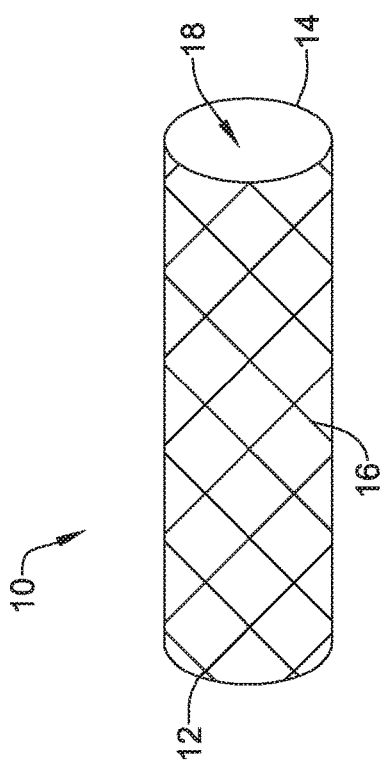

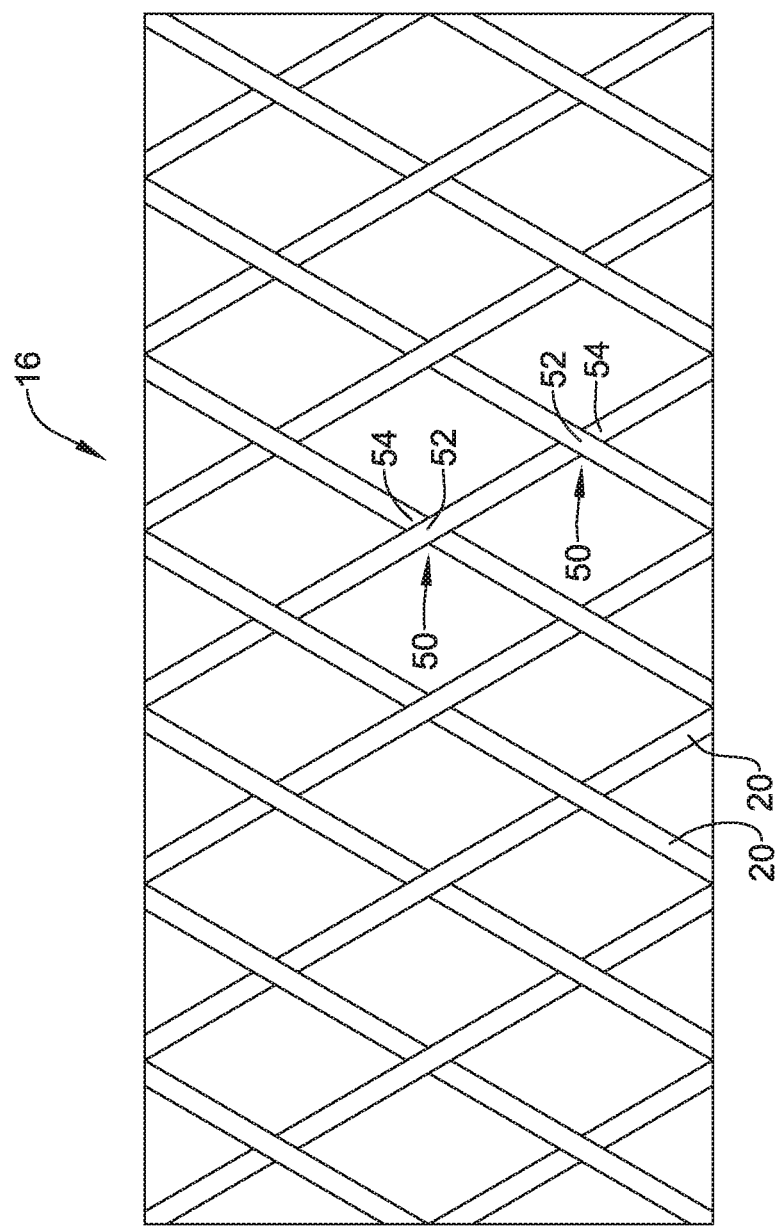

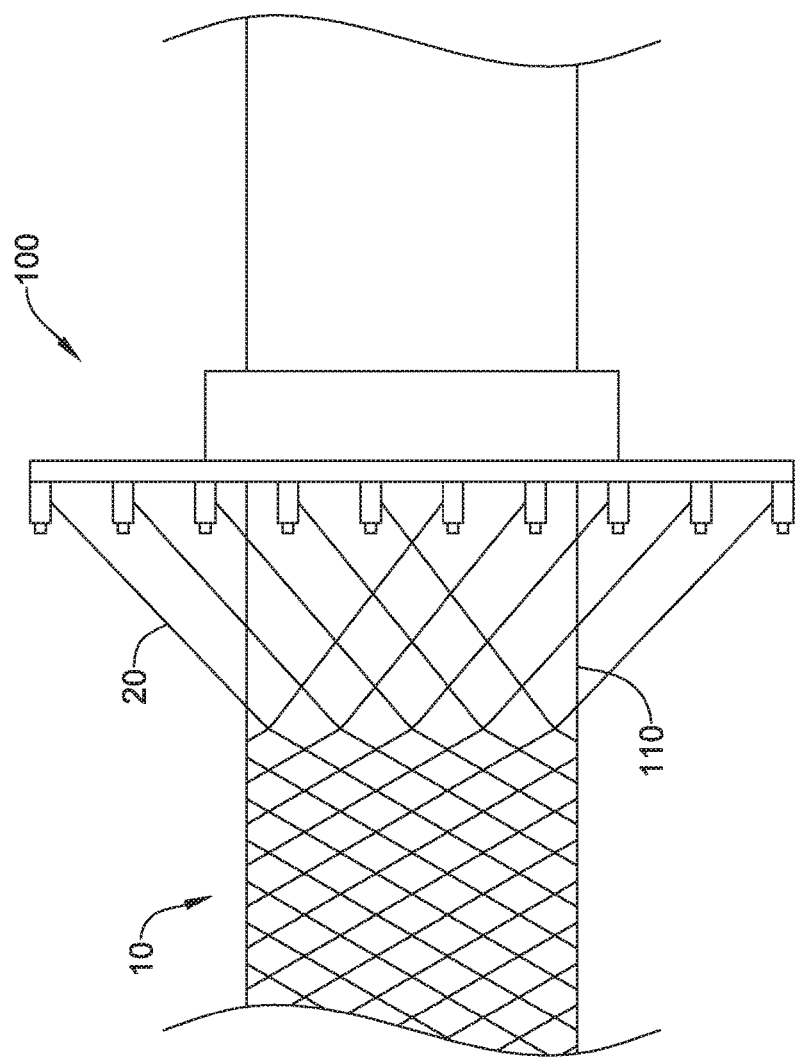

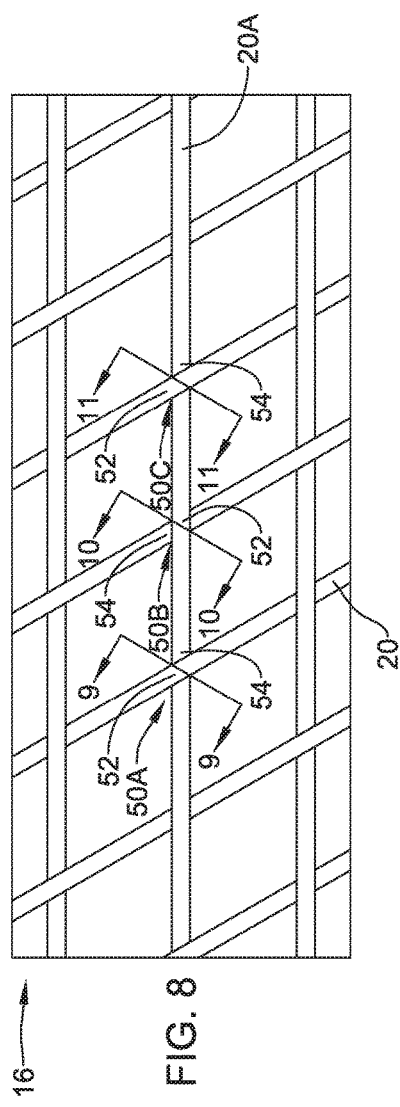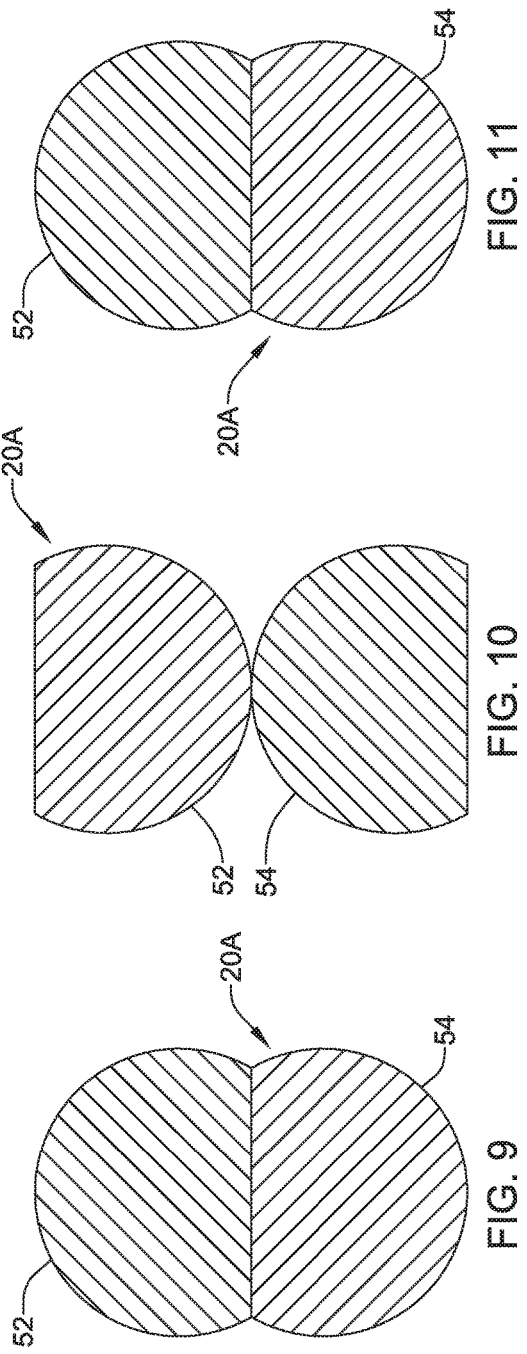

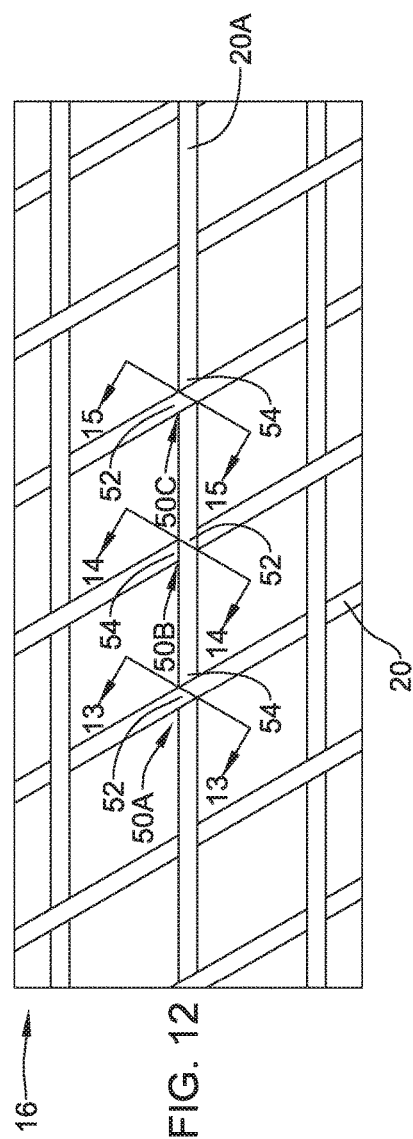
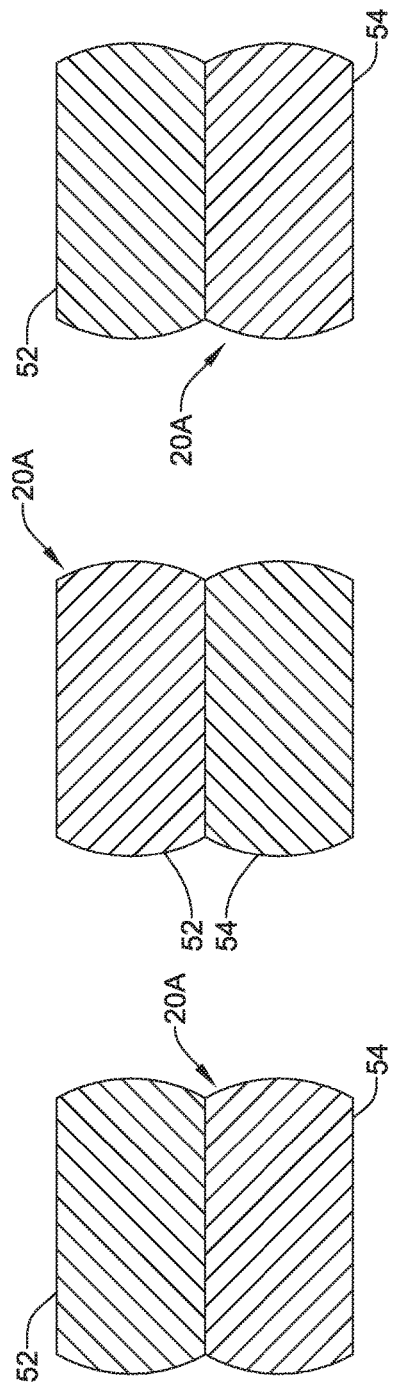

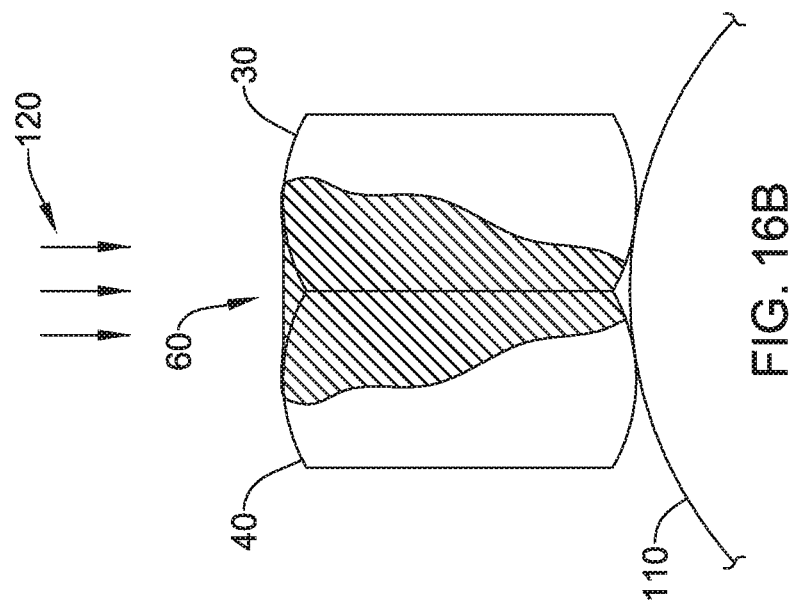
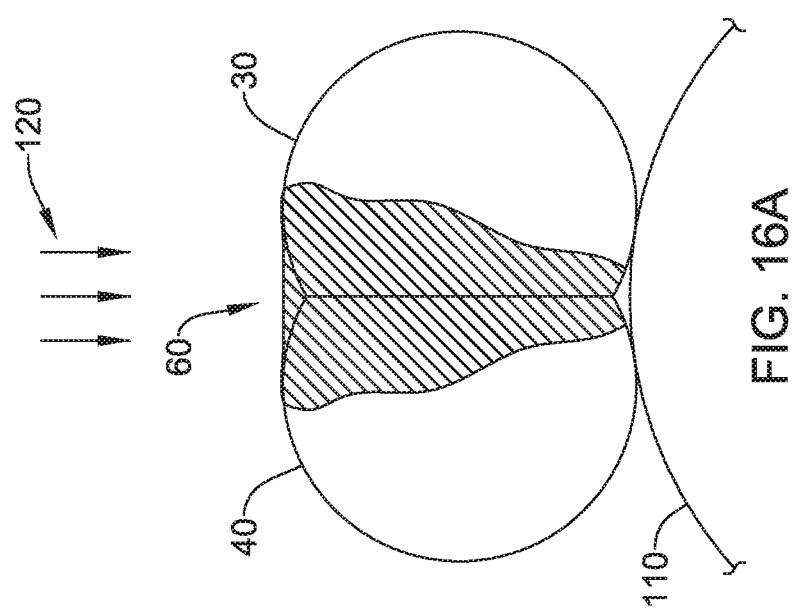

BRAIDED STENT AND METHOD OF MANUFACTURING A BRAIDED STENT

CROSS-REFERENCE TO RELATED APPLICATIONS

This application claims the benefit of priority under 35 U.S.C. § 119 to U.S. Provisional Application No. 62/296,503, filed Feb. 17, 2016, the entirety of which is incorporated herein by reference.

TECHNICAL FIELD

The present disclosure pertains to medical devices, such as an endoprosthesis or stent, and methods for manufacturing and/or using said medical devices.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal, gastrointestinal, or renal tracts, or to position a device such as an artificial valve or filter within a body lumen, in some instances. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and uses thereof.

In a first example, a stent actuatable between a delivery configuration and a deployed configuration may comprise one or more interwoven filaments each including a cross-sectional profile having at least one flattened portion, wherein a flattened portion of a first filament portion of the one or more filaments is positioned in contact with a flattened portion of a second filament portion of the one or more filaments.

In addition or alternatively, the flattened portion of the first filament portion of the one or more filaments is fixedly attached to the flattened portion of the second filament portion of the one or more filaments.

In addition or alternatively, the flattened portion of the first filament portion of the one or more filaments is welded to the flattened portion of the second filament portion of the one or more filaments.

In addition or alternatively, the flattened portion of the first filament portion of the one or more filaments includes a first flat surface and the flattened portion of the second filament portion of the one or more filaments includes a second flat surface, the first flat surface being oriented facing the second flat surface.

In addition or alternatively, the first flat surface extends less than half way around a circumference of the first filament portion of the one or more filaments and the second flat surface extends less than half way around a circumference of the second filament portion of the one or more filaments.

In another example, a method of manufacturing a stent may comprise interweaving one or more filaments around a stent mandrel, the one or more filaments each including a cross-sectional profile having at least one flattened portion, and positioning a flattened portion of a first filament portion of the one or more filaments facing a flattened portion of a second filament portion of the one or more filaments.

In addition or alternatively, the method may further include the step of welding the flattened portion of the first filament portion of the one or more filaments to the flattened portion of the second filament portion of the one or more filaments.

In addition or alternatively, the step of welding includes at least partially melting the flattened portion of the first filament portion of the one or more filaments and the flattened portion of the second filament portion of the one or more filaments to form a weld joint therebetween.

In addition or alternatively, positioning the flattened portion of the first filament portion of the one or more filaments facing the flattened portion of the second filament portion of the one or more filaments includes vibrating the stent mandrel to orient the flattened portion of the first filament portion of the one or more filaments facing the flattened portion of the second filament portion of the one or more filaments.

In addition or alternatively, the one or more filaments each include a generally round cross-sectional profile modified to form the at least one flattened portion.

In addition or alternatively, the at least one flattened portion is ground into the generally round cross-sectional profile.

In addition or alternatively, the at least one flattened portion is rolled into the generally round cross-sectional profile.

In addition or alternatively, the cross-sectional profile defines a perimeter and each flattened portion extends around less than half of the perimeter.

In addition or alternatively, the interweaving step includes forming a plurality of crossing points, each of the plurality of crossing points being formed by an upper filament portion of the one or more filaments crossing over a lower filament portion of the one or more filaments.

In addition or alternatively, a flattened portion of the lower filament portion faces a flattened portion of the upper filament portion at each of the plurality of crossing points.

In another example, a method of manufacturing a stent may comprise interweaving one or more filaments, each including a cross-sectional profile having at least one flattened portion, around a stent mandrel such that a plurality of crossing points are formed, each of the plurality of crossing points being formed by a lower filament portion and an upper filament portion, orienting a flattened portion of the lower filament portion to face a flattened portion of the upper filament portion at each of the plurality of crossing points, and applying heat energy to a first filament portion of the one or more filaments and a second filament portion of the one or more filaments, the first filament portion having a flattened portion facing a flattened portion of the second filament portion, to form a weld joint between the first filament portion and the second filament portion.

In addition or alternatively, orienting the flattened portion of the lower filament portion to face the flattened portion of the upper filament portion at each of the plurality of crossing points includes vibrating the stent mandrel.

In addition or alternatively, orienting the flattened portion of the lower filament portion to face the flattened portion of the upper filament portion at each of the plurality of crossing points includes reversibly actuating the stent between a generally elongated configuration and a generally shortened configuration.

In addition or alternatively, applying heat energy includes focusing a laser beam on the first filament portion and the second filament portion.

In addition or alternatively, the flattened portion of the first filament portion abuts the flattened portion of the second filament portion.

The above summary of some embodiments, aspects, and/or examples is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 1 illustrates an example stent in a delivery configuration;

FIG. 2 illustrates the example stent of FIG. 1 in a deployed configuration;

FIG. 3 is an enlarged view illustrating a portion of the stent of FIG. 1 taken along the line 3-3;

FIG. 7 is a side view of a portion of an example braiding machine manufacturing an example stent;

FIG. 8 is an enlarged view illustrating a portion of an example stent;

FIG. 9 is a cross-sectional view of an example configuration of the stent of FIG. 8 taken along the line 9-9;

FIG. 10 is a cross-sectional view of an example configuration of the stent of FIG. 8 taken along the line 10-10;

FIG. 11 is a cross-sectional view of an example configuration of the stent of FIG. 8 taken along the line 11-11;

FIG. 12 is enlarged view illustrating a portion of an example stent;

FIG. 13 is a cross-sectional view of an example configuration of the stent of FIG. 12 taken along the line 13-13;

FIG. 14 is a cross-sectional view of an example configuration of the stent of FIG. 12 taken along the line 14-14;

FIG. 15 is a cross-sectional view of an example configuration of the stent of FIG. 12 taken along the line 15-15;

FIG. 16A is a cross-sectional view illustrating an example weld joint in the example configuration of the stent of FIG. 5A; and FIG. 16B is a cross-sectional view illustrating an example weld joint in the example configuration of the stent of FIG. 5B;

Figure 4:
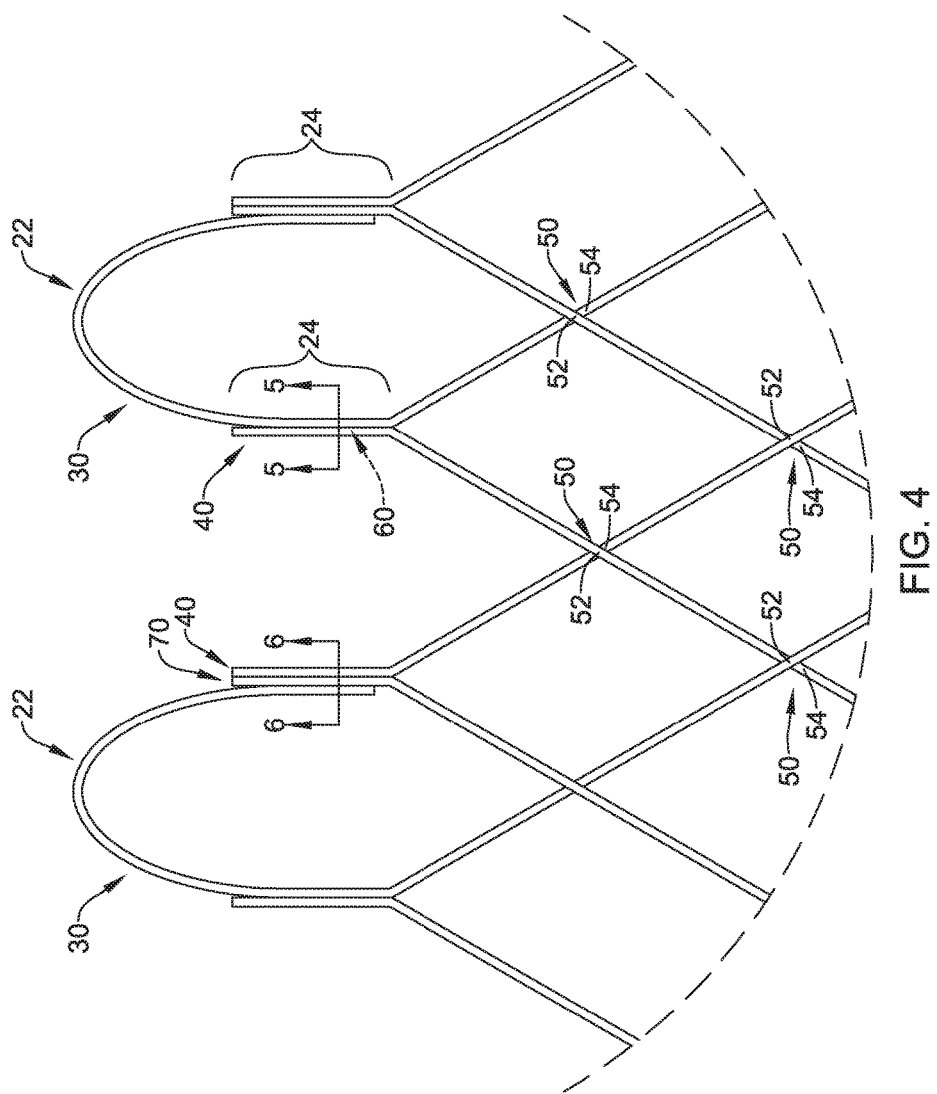
FIG. 4 is an enlarged view illustrating a portion of an end of the stent of FIG. 1.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

An exemplary implantable endoprosthesis may be configured to be positioned in a body lumen for a variety of medical applications. For example, the endoprosthesis may be used to treat a stenosis in a blood vessel, used to maintain a fluid opening or pathway in the vascular, urinary, biliary, tracheobronchial, esophageal, gastrointestinal, or renal tracts, or position a device such as an artificial valve or filter within a body lumen, in some instances. In some instances, the endoprosthesis may be a prosthetic graft, a stent-graft, or a stent (e.g., a vascular stent, tracheal stent, bronchial stent, esophageal stent, gastrointestinal stent, biliary stent, etc.). For the purposes of this disclosure, the terms "endoprosthesis" and "stent" may generally be used interchangeably. Although illustrated herein as a stent 10, the endoprosthesis may be any of a number of devices that may be introduced endoscopically, subcutaneously, percutaneously, or surgically to be positioned within an organ, tissue, or lumen, such as a heart, artery, vein, urethra, esophagus, trachea, bronchus, bile duct, or the like.

FIGS. 1-2 illustrate an exemplary stent 10 as a hollow, self-expanding, interwoven tubular structure including an open first end 12, an open second end 14 opposite the first end 12 and defining a length therebetween, a tubular wall 16 extending longitudinally between the first end 12 and the second end 14, a lumen 18 extending therethrough, an outer diameter defining an outer surface of the tubular wall 16, and an inner diameter defining an inner surface of the tubular wall 16 forming the lumen 18 extending therethrough. It should be noted that some features of the stent 10 are either not shown, or are shown schematically, in FIGS. 1-2 for simplicity. Additional details regarding some of the components of the stent 10 may be provided in other figures in greater detail.

In some embodiments, the stent 10, which may be a self-expanding stent, may be configured to automatically actuate and/or expand from a compressed delivery configuration, as seen in FIG. 1, to an expanded deployed configuration, as seen in FIG. 2, upon the removal of a constraining force acting on the stent 10. In some embodiments, the constraining force may be applied or provided by one or more of a variety of structures as is known in the art (e.g., a delivery sheath, a restraining element, a tether, an actuation filament or wire, etc.). In some embodiments, the stent 10 may be a mechanically expandable braided or knitted stent configured to be actuated and/or expanded from a compressed delivery configuration to an expanded deployed configuration through the application of a mechanical force acting on the stent 10 (e.g., a radially expanding structure, such as a balloon, disposed therein). In some embodiments, the stent 10 may be configured to automatically expand from the compressed delivery configuration to the expanded deployed configuration upon the removal of the constraining force acting on the stent 10 (e.g., due to phase change of a shape memory material, stored spring force, etc.). In some embodiments, the stent 10 may be a self-expanding and/or self-actuating braided or knitted stent. In some embodiments, the stent 10 may require an external input (e.g., an externally generated or applied force, an actuation force or trigger, manual manipulation by a user, an applied thermal stimulus, an applied electrical stimulus, other applied stimulus, etc.) in order to actuate and/or expand from the compressed delivery configuration to the expanded deployed configuration. In some embodiments, the stent 10 may be configured to reversibly expand from the compressed delivery configuration to the expanded deployed configuration.

A portion of the tubular wall 16 is depicted in FIG. 3 as having one or more filaments 20 forming the tubular wall 16. In some embodiments, the one or more filaments 20 may comprise one individual filament, two individual filaments, three individual filaments, four individual filaments, or another suitable number of individual filaments (e.g., five, eight, ten, twelve, sixteen, thirty-two etc.). In some embodiments, the one or more filaments 20 may extend along a longitudinal length of the stent 10 and/or the tubular wall 16. In some embodiments, the one or more filaments 20 may be arranged helically, spirally, angled circumferentially, or another suitable arrangement.

In some embodiments, the one or more filaments 20 may be formed into the tubular wall 16 by interweaving the one or more filaments 20, braiding the one or more filaments 20, winding the one or more filaments 20, knitting the one or more filaments 20, and/or combinations thereof. In some embodiments, the one or more filaments 20 may form a plurality of crossing points 50 when interwoven together and/or formed into the tubular wall 16, wherein each of the plurality of crossing points 50 is formed by an upper filament portion 52 of the one or more filaments 20 (i.e., a radially outwardly positioned filament portion) crossing over a lower filament portion 54 of the one or more filaments 20 (i.e., a radially inwardly positioned filament portion). In at least some embodiments, the one or more filaments 20 may preferably be braided to form the tubular wall 16 of the stent 10, such as by an example braiding machine 100 shown illustratively in FIG. 7, as will be described in more detail below. In some embodiments, the one or more filaments 20 may be a single filament knitted to form the tubular wall 16 of the knitted stent 10, such as by an example knitting machine. In some embodiments, the stent 10 may include one plurality of crossing points 50, or the stent 10 may include more than one plurality of crossing points 50 and/or additional pluralities of crossing points 50. In some embodiments, all of the pluralities of crossing points 50 may include similar characteristics, structure, and/or features, or some of the pluralities of crossing points 50 may include differing characteristics, structure, and/or features.

As used herein, the outer surface of the tubular wall 16 is intended to refer to a radially outward facing surface of the one or more filaments 20 commensurate with the outer diameter of the stent 10 and/or the tubular wall 16. As used herein, the inner surface is intended to refer to a radially inward facing surface of the one or more filaments 20 commensurate with the inner diameter of the stent 10 and/or the tubular wall 16. In some embodiments, the stent 10 may be substantially cylindrical and/or tubular in shape or configuration. In some embodiments, the stent 10 and/or the tubular wall 16 may define a central longitudinal axis extending therethrough along a fluid flow path or passage through the lumen 18. Other shapes and/or configurations are also contemplated.

In some embodiments, the one or more filaments 20 may be arranged to form a first end 12 and/or a second end 14 of the stent 10 and/or the tubular wall 16. In some embodiments, the one or more filaments 20 at the first end 12 may be substantially similar to and/or a mirror image of the one or more filaments 20 at the second end 14. In some embodiments, one or more filaments 20 at the first end 12 may be arranged differently than at the second end 14. FIG. 4 illustrates an example arrangement for an end (e.g., the first end 12 and/or the second end 14) of the stent 10 and/or the tubular wall 16.

In some embodiments, as may be seen in FIG. 4 for example, the one or more filaments 20 may include a first filament portion 30, a second filament portion 40, and/or a third filament portion 70. The first filament portion 30 may be an end region of a first filament of the one or more filaments 20, the second filament portion 40 may be an end region of a second filament of the one or more filaments 20, and the third filament portion 70 may be an end region of a third filament of the one or more filaments 20. In some embodiments, the one or more filaments 20 may include fewer or additional filament portions. For simplicity and brevity, arrangements comprising the first filament portion 30, the second filament portion 40, and/or the third filament portion 70 may be expressly discussed herein. Other configurations and arrangements are contemplated within the scope of this disclosure.

In some embodiments, the first filament portion 30, the second filament portion 40, and/or the third filament portion 70 may be arranged as terminatingly adjacent filaments at, near, and/or adjacent to the first end 12 and/or the second end 14. In some embodiments, one of the first filament portion 30, the second filament portion 40, and the third filament portion 70 may be arranged to extend longitudinally beyond an end of the other of the first filament portion 30, the second filament portion 40, and the third filament portion 70 and be looped back inward toward a central portion of the tubular wall 16 to form an atraumatic loop 22. In some embodiments, a flattened portion of the first filament portion 30, the second filament portion 40, and/or the third filament portion 70 may be positioned in contact with a flattened portion of the first filament portion 30, the second filament portion 40, and/or the third filament portion 70 at and/or adjacent to the first end 12 and/or the second end 14. In some embodiments, one filament portion, for example the third filament portion 70, and/or a flattened portion thereof, may be positioned in contact with and/or adjacent to a flattened portion of more than one other filament portion.

Figure 5A:
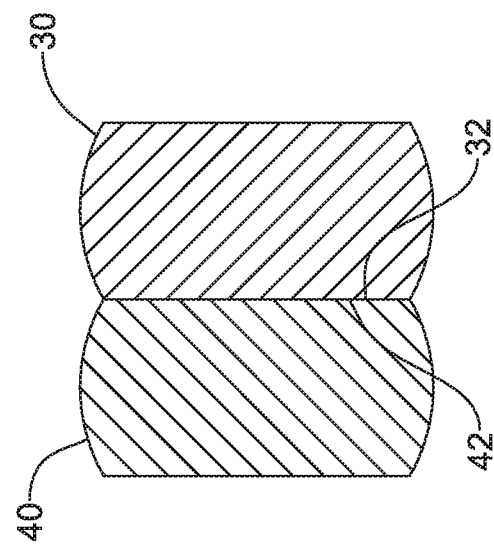
FIG. 5A is a cross-sectional view of an example configuration of the stent of FIG. 4 taken along the line 5-5.
Figure 5B:
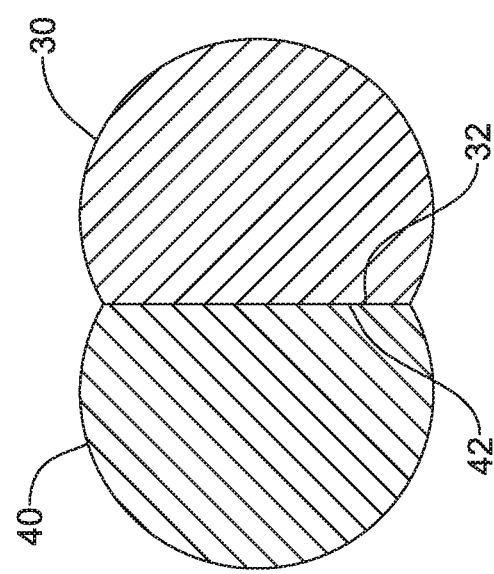
FIG. 5B is an alternative cross-sectional view of an example configuration of the stent of FIG. 4 taken along the line 5-5.
Figure 6A:
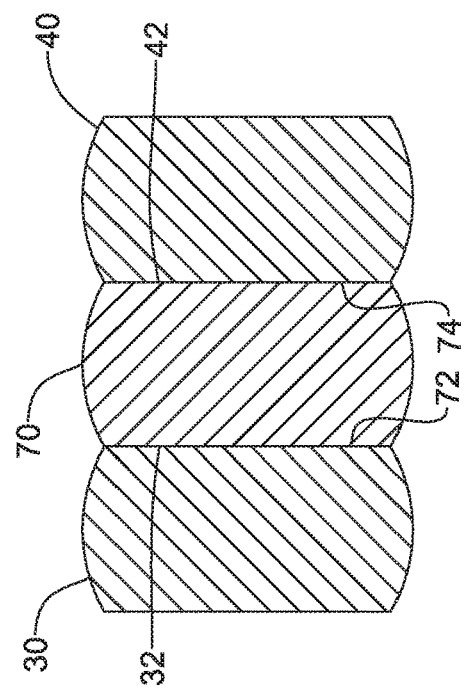
FIG. 6A is a cross-sectional view of an example configuration of the stent of FIG. 4 taken along the line 6-6.
Figure 6B:
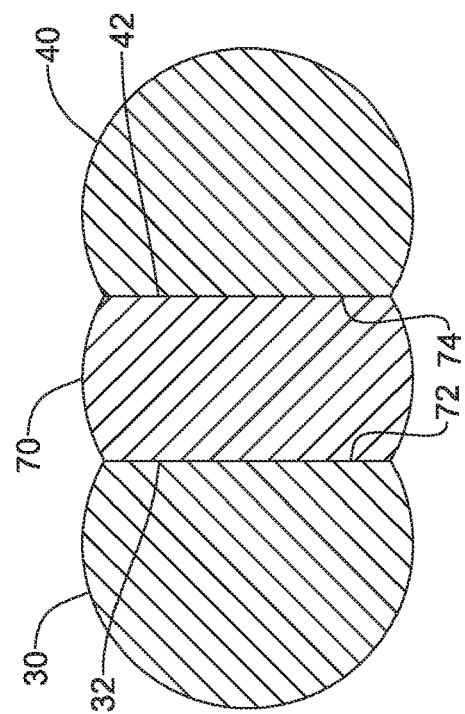
FIG. 6B is an alternative cross-sectional view of an example configuration of the stent of FIG. 4 taken along the line 6-6.

In some embodiments, the first filament portion 30, the second filament portion 40, and/or the third filament portion 70 may each include a cross-sectional profile having at least one flattened portion, as illustrated in FIGS. 5A, 5B, 6A, and 6B for example. In some embodiments, the first filament portion 30, the second filament portion 40, and/or the third filament portion 70 may each include more than one flattened portion (e.g., two flattened portions, three flattened portions, etc.), as seen in FIGS. 5B, 6A, and 6B for example. In some embodiments, a flattened portion of the first filament portion 30 may include a first flat surface 32. In some embodiments, a flattened portion of the second filament portion 40 may include a second flat surface 42. In some embodiments, the third filament portion 70 may include a third flat surface 72 and a fourth flat surface 74. In at least some embodiments, some, each, and/or all of the flattened portions may include one or more flat surfaces, and in some embodiments may include two flat surfaces, three flat surfaces, etc. In some embodiments, the at least one flattened portion of the first filament portion 30, the at least one flattened portion of the second filament portion 40, and/or the at least one flattened portion of the third filament portion 70 may extend along a portion of a length of the one or more filaments 20 and/or the longitudinal length of the stent 10. In some embodiments, the at least one flattened portion of the first filament portion 30, the at least one flattened portion of the second filament portion 40, and/or the at least one flattened portion of the third filament portion 70 may extend along an entire length of the corresponding filament of the one or more filaments 20 and/or the entire longitudinal length of the stent 10.

In some embodiments, the first flat surface 32 may extend less than half way around a circumference of the first filament portion 30. In some embodiments, the first flat surface 32 may extend less than 40% of a total circumference of the first filament portion 30. In some embodiments, the first flat surface 32 may extend less than 30% of a total circumference of the first filament portion 30. In some embodiments, the first flat surface 32 may extend less than 20% of a total circumference of the first filament portion 30.

In some embodiments, the second flat surface 42 may extend less than half way around a circumference of the second filament portion 40. In some embodiments, the second flat surface 42 may extend less than 40% of a total circumference of the second filament portion 40. In some embodiments, the second flat surface 42 may extend less than 30% of a total circumference of the second filament portion 40. In some embodiments, the second flat surface 42 may extend less than 20% of a total circumference of the second filament portion 40.

In some embodiments, the third flat surface 72 may extend less than half way around a circumference of the third filament portion 70. In some embodiments, the third flat surface 72 may extend less than 40% of a total circumference of the third filament portion 70. In some embodiments, the third flat surface 72 may extend less than 30% of a total circumference of the third filament portion 70. In some embodiments, the third flat surface 72 may extend less than 20% of a total circumference of the third filament portion 70. In some embodiments, the fourth flat surface 74 may extend less than half way around a circumference of the third filament portion 70.

In some embodiments, the fourth flat surface 74 may extend less than 40% of a total circumference of the third filament portion 70. In some embodiments, the fourth flat surface 74 may extend less than 30% of a total circumference of the third filament portion 70. In some embodiments, the fourth flat surface 74 may extend less than 20% of a total circumference of the third filament portion 70.

Other configurations are also contemplated, including, but not limited to, the flat surface(s) extending halfway or more than halfway (e.g., greater than 50%) around the total circumference of the respective filament portion(s). In some embodiments, the cross-sectional profile having at least one flattened portion may define a perimeter, and each flattened portion may extend around less than half of the perimeter. Other configurations are also contemplated.

As mentioned above, in some embodiments, a flattened portion of the first filament portion 30 may be juxtaposed with and/or positioned in abutting contact with a flattened portion of the second filament portion 40 and/or a flattened portion of the third filament portion 70 at and/or adjacent to the first end 12 and/or the second end 14, for example at an abutting region 24. In some embodiments, the first flat surface 32 may be oriented facing the second flat surface 42, the third flat surface 72, and/or the fourth flat surface 74 in the abutting region 24. In some embodiments, the first flat surface 32 may be in abutting and/or direct contact with the second flat surface 42, the third flat surface 72, and/or the fourth flat surface 74 in the abutting region 24. In some embodiments, the flattened portion and/or the first flat surface 32 of the first filament portion 30 may be oriented substantially parallel to the flattened portion and/or the second flat surface 42 of the second filament portion 40, and/or the flattened portion and/or the third flat surface 72 of the third filament portion 70 and/or the fourth flat surface 74 of the third filament portion 70. In some embodiments, the flattened portion and/or the first flat surface 32 of the first filament portion 30 may be oriented within about plus or minus 10 degrees of parallelism to the flattened portion and/or the second flat surface 42 of the second filament portion 40 and/or the flattened portion and/or the third flat surface 72 of the third filament portion 70 and/or the fourth flat surface 74 of the third filament portion 70.

In some embodiments, a flattened portion of the third filament portion 70 may be juxtaposed with and/or positioned in abutting contact with a flattened portion of first filament portion 30 and a flattened portion of the second filament portion 40, for example at an abutting region 24. In some embodiments, the third flat surface 72 may be oriented facing the first flat surface 32 and the fourth flat surface 74 may be oriented facing the second flat surface 42 in the abutting region 24. In some embodiments, the third flat surface 72 may be in abutting and/or direct contact with the first flat surface 32 and the fourth flat surface 74 may be in abutting and/or direct contact with the second flat surface 42 in the abutting region 24.

In some embodiments, the flattened portion of the first filament portion 30 may be fixedly attached to the flattened portion of the second filament portion 40 and/or the flattened portion of the third filament portion 70 in the abutting region 24. In some embodiments, the flattened portion of the first filament portion 30 may be welded to the flattened portion of the second filament portion 40 and/or the flattened portion of the third filament portion 70 at a weld joint 60 disposed in the abutting region 24. In some embodiments, the first flat surface 32 may be welded to the second flat surface 42, the third flat surface 72, and/or the fourth flat surface 74 at a weld joint 60 in the abutting region 24. In some embodiments, the weld joint(s) 60 may include only one weld or a plurality of welds. In some embodiments, all weld joints 60 present in the stent 10 may be arranged and/or oriented such that a flat surface of one filament portion is facing and/or abutting a flat surface of another filament portion in an abutting region, wherein the flat surfaces and/or the filament portions are welded together in the abutting regions. Other configurations are also contemplated. In some embodiments, the weld joint(s) 60 may be formed more easily and/or completely as a result of the arrangement of the flat surfaces. For example, in some embodiments, alignment and/or abutment of the flat surfaces may promote more even heating, melting, and/or comingling of material(s) within the weld joint and/or the weld melt pool formed when making the weld joint. In some embodiments, alignment and/or abutment of the flat surfaces may form a smoother and/or more complete weld joint free of holes and/or voids within the weld joint, for example, when the weld melt pool cools and/or solidifies.

In some embodiments, a method of manufacturing a stent 10 may include producing, obtaining, forming, and/or making one or more filaments 20, each of the one or more filaments 20 including a cross-sectional profile having at least one flattened portion. In some embodiments, producing, obtaining, forming, and/or making one or more filaments 20 each including a cross-sectional profile having at least one flattened portion may include modifying one or more filaments 20 having a generally round cross-sectional profile to include and/or form at least one flattened portion. In some embodiments, modifying one or more filaments 20 may include grinding the generally round cross-sectional profile to include and/or form at least one flattened portion. In some embodiments, modifying one or more filaments 20 may include rolling the generally round cross-sectional profile to include and/or form at least one flattened portion. In some embodiments, modifying one or more filaments 20 may include cutting the generally round cross-sectional profile to include and/or form at least one flattened portion. In some embodiments, modifying one or more filaments 20 may include stamping or forging the generally round cross-sectional profile to include and/or form at least one flattened portion. In some embodiments, chemical modification (e.g., etching, dissolution, etc.) may be applied to the generally round cross-sectional profile to include and/or form at least one flattened portion. In some embodiments, other suitable processes may be utilized to create the cross-sectional profile having at least one flattened portion. For example, in some embodiments, producing, obtaining, forming, and/or making one or more filaments 20 each including a cross-sectional profile having at least one flattened portion may include extruding, pulling, drawing, and/or other similar processes a material through a die or other forming tool to produce the cross-sectional profile having at least one flattened portion directly, without further mechanical, chemical, or other modification.

In some embodiments, a method of manufacturing a stent 10 may include interweaving (e.g., braiding, wrapping, knitting, etc.) one or more filaments 20 around a stent mandrel 110, as seen in FIG. 7 for example, the one or more filaments 20 each including a cross-sectional profile having at least one flattened portion. In some embodiments, the one or more filaments 20 may be a single continuous filament interwoven with itself. In some embodiments, the one or more filaments 20 may be a plurality of filaments interwoven around the mandrel sequentially, simultaneously, and/or a combination thereof. In some embodiments, the stent mandrel 110 may include a plurality of mandrel projections extending radially outward therefrom. In some embodiments, the plurality of mandrel projections may be arranged, oriented, and/or organized such that the one or more filaments 20 lie in a predetermined arrangement. In some embodiments, the plurality of mandrel projections may be arranged, oriented, and/or organized such that the one or more filaments 20 must lie in the predetermined arrangement. In some embodiments, the plurality of mandrel projections and/or the predetermined arrangement may position the one or more filaments 20 into a desired orientation.

In some embodiments, a method of manufacturing a stent 10 may include interweaving (e.g., braiding, wrapping, knitting, etc.) the one or more filaments 20 around a stent mandrel 110 such that a plurality of crossing points 50 are formed, each of the plurality of crossing points 50 being formed by a lower filament portion 54 and an upper filament portion 52 disposed above and/or crossing over the lower filament portion 54. In general, the one or more filaments 20 may be arranged in an undulating and/or repeating over and under relationship, as will be explained further below. In some embodiments, a flattened portion of the lower filament portion 54 may face and/or abut a flattened portion of the upper filament portion 52 at each of the plurality of crossing points 50. Examples of the plurality of crossing points 50 may be seen in FIGS. 8 and 12, and example orientations of the one or more filaments 20 at the crossing points 50 may be seen in FIGS. 9-11 and 13-15. When multiple filaments are braided in an over-under pattern, a first filament may form an upper filament portion 52 at a first crossing point 50 while the first filament may form a lower filament portion 54 at a second, adjacent (consecutive) crossing point 50, and then may again form an upper filament portion 52 at a third, adjacent (consecutive) crossing point 50. Thus a first filament may alternate between upper and lower filament portions at consecutive crossing points 50. It follows that a second filament, as well as additional filaments braided in an over-under pattern, may alternate between upper and lower filament portions at consecutive crossing points 50.

The undulating and/or repeating over and under relationship of the one or more filaments 20 being interwoven around the stent mandrel 110 may create a varying configuration and/or arrangement of the one or more filaments 20, as seen in FIGS. 3-4 and 8-15 for example. For example, in some embodiments, the first filament portion 30 may form and/or be coincident with the upper filament portion 52, and in some embodiments, the first filament portion 30 may form and/or be coincident with the lower filament portion 54, depending on which crossing point 50 is being examined. Similarly, in some embodiments, the second filament portion 40 may form and/or be coincident with the lower filament portion 54, and in some embodiments, the second filament portion 40 may form and/or be coincident with the upper filament portion 52, depending on which crossing point 50 is being examined. In other words, a single filament 20A may form an upper filament portion 52 at one crossing point 50 and a lower filament portion 54 at another crossing point 50, as evidenced by the cross-hatching shown in the cross-sectional views of FIGS. 9-11 and 13-15. To illustrate an example, a single filament 20A may form the lower filament portion 54 at a first crossing point 50A in FIGS. 9 and 13, pass over another and/or adjacent filament 20 (or filament portion) to form the upper filament portion 52 at an adjacent and/or second crossing point 50B in FIGS. 10 and 14, and then pass under another and/or adjacent filament 20 (or filament portion) to form the lower filament portion 54 at an adjacent and/or third crossing point 50C in FIGS. 11 and 15. In some embodiments, orienting one flattened portion of a lower filament portion 54 to face one flattened portion of an upper filament portion 52 at each of the plurality of crossing points 50 may include twisting or rotating one or both filament portions 52, 54 from its orientation at adjacent crossing points 50, such as twisting or rotating the filament portions 52, 54 180 degrees about its longitudinal axis from its orientation at adjacent crossing points 50. As such, these terms (e.g., first, second, upper, lower, etc.) may be considered relative and the positioning of the features may depend upon which portion of the stent 10 is being examined or how the stent 10 is being observed.

In some embodiments, a method of manufacturing a stent 10 may include positioning a flattened portion of a first filament portion 30 of the one or more filaments 20 facing a flattened portion of a second filament portion 40 of the one or more filaments 20, as seen in FIGS. 4-5B and FIGS. 8-15, for example. In some embodiments, the flattened portion of the first filament portion 30 and the flattened portion of the second filament portion 40 may be at and/or adjacent to the first end 12 and/or the second end 14 of the stent 10. In some embodiments, the flattened portion of the first filament portion 30 may extend along a portion of a filament 20 or along an entire length of a filament 20. In some embodiments, the flattened portion of the second filament portion 40 may extend along a portion of a filament 20 or along an entire length of a filament 20. In some embodiments, the first filament portion 30 and the second filament portion 40 may be substantially mirror images of each other. In some embodiments, the first filament portion 30 and the second filament portion 40 may be configured differently (e.g., may have different flattened portions, sizing, length, magnitude of features, etc.) from each other.

In some embodiments, the plurality of mandrel projections and/or the predetermined arrangement may only permit the flattened portion of the first filament portion 30 and the flattened portion of the second filament portion 40 to fit between adjacent mandrel projections when positioned in the desired orientation (e.g., the flattened portion of the first filament portion 30 facing and/or abutting the flattened portion of the second filament portion 40, for example). In some embodiments, positioning the flattened portion of the first filament portion 30 facing the flattened portion of the second filament portion 40 may include vibrating the stent mandrel with the first and second filament portions 30, 40 arranged around the mandrel to orient the flattened portion of the first filament portion 30 facing the flattened portion of the second filament portion 40. In some embodiments, positioning the flattened portion of the first filament portion 30 facing the flattened portion of the second filament portion 40 may include orienting the flattened portion of the first filament portion 30 facing the flattened portion of the second filament portion 40 generally normal to a central longitudinal axis of the stent mandrel 110. In at least some of these embodiments, the flattened portion of the first filament portion 30 facing the flattened portion of the second filament portion 40 may be disposed and/or positioned at and/or adjacent to the first end 12 and/or the second end 14 of the stent 10, for example, in the abutting region 24. In some embodiments, a method of manufacturing a stent 10 may include orienting one flattened portion of a lower filament portion 54 to face one flattened portion of an upper filament portion 52 at a plurality of crossing points 50, as seen in FIGS. 8-15, for example.

In some embodiments, a method of manufacturing a stent 10 may include orienting one flattened portion of a lower filament portion 54 to face one flattened portion of an upper filament portion 52 at each of the plurality of crossing points 50, as seen in FIGS. 12-15, for example. In some embodiments, orienting one flattened portion of a lower filament portion 54 to face one flattened portion of an upper filament portion 52 at each of the plurality of crossing points 50 may include vibrating the stent mandrel 110 with the upper and lower filament portions 52, 54 arranged around the mandrel 110. In some embodiments, orienting one flattened portion of a lower filament portion 54 to face one flattened portion of an upper filament portion 52 at each of the plurality of crossing points 50 may include reversibly actuating the stent 10 between a generally elongated and/or a compressed delivery configuration, and a generally shortened and/or expanded deployed configuration. In some embodiments, orienting one flattened portion of a lower filament portion 54 to face one flattened portion of an upper filament portion 52 at each of the plurality of crossing points 50 may include twisting or rotating one or both filament portions 52, 54 from its orientation at adjacent crossing points 50, such as twisting or rotating the filament portions 52, 54 180 degrees about its longitudinal axis from its orientation at adjacent crossing points 50.

In some embodiments, orienting one flattened portion of a lower filament portion to face one flattened portion of an upper filament portion at some or each of the plurality of crossing points may result in an interwoven (e.g., braided or knitted) stent that may permit the use of a smaller and/or narrower profile delivery system. For example, in some embodiments, orienting one flattened portion of a lower filament portion to face one flattened portion of an upper filament portion at some or each of the plurality of crossing points may create an interwoven stent having a reduced radial thickness for the tubular wall and/or a reduced overall or outer diameter of the tubular wall compared to a stent having the same inner diameter made using filaments without flattened portions (e.g., round wires, filaments, etc.). Accordingly, a reduced profile (e.g., reduced diameter, etc.) delivery device may be used to deliver the stent to the treatment site.

In some embodiments, a method of manufacturing a stent 10 may include welding the flattened portion of the first filament portion 30 of the one or more filaments 20 to the flattened portion of the second filament portion 40 of the one or more filaments 20 and/or the flattened portion of the third filament portion 70 of the one or more filaments 20. In some embodiments, welding the flattened portion of the first filament portion 30 of the one or more filaments 20 to the flattened portion of the second filament portion 40 of the one of more filaments 20 and/or the flattened portion of the third filament portion 70 of the one or more filaments 20 may include at least partially melting the flattened portion of the first filament portion 30 of the one or more filaments 20, the flattened portion of the second filament portion 40 of the one or more filaments 20, and/or the flattened portion of the third filament portion 70 of the one or more filaments 20 to form a weld joint 60 therebetween, as seen in FIGS. 16A and 16B, for example.

In some embodiments, a method of manufacturing a stent 10 may include applying heat energy 120 to a first filament portion 30 of the one or more filaments 20, a second filament portion 40 of the one or more filaments 20, and/or a third filament portion 70 of the one or more filaments 20, the first filament portion 30 having a flattened portion juxtaposed with or facing a flattened portion of the second filament portion 40 and/or a flattened portion of the third filament portion 40, to form a weld joint 60 between the first filament portion 30, the second filament portion 40, and/or the third filament portion 70. In some embodiments, the flattened portion of the first filament portion 30 may abut the flattened portion of the second filament portion 40 and/or the flattened portion of the third filament portion 70. In some embodiments, applying heat energy 120 to the first filament portion 30 of the one or more filaments 20, the second filament portion 40 of the one or more filaments 20, and/or the third filament portion 70 of the one or more filaments 20 may include focusing a laser beam on the first filament portion 30, the second filament portion 40, the third filament portion 70, and/or at the intended weld joint 60. In some embodiments, heat energy 120 and/or a laser beam may be focused on the first filament portion 30, the second filament portion 40, the third filament portion 70, and/or at the intended weld joint 60, in a direction normal to a central longitudinal axis of the stent mandrel 110 and/or along a radial line extending from the central longitudinal axis of the stent mandrel 110.

In some embodiments, a stent 10 may include one or more weld joints 60. For example, a stent 10 (e.g., a kitted stent) having only one filament 20 may require only one weld joint 60, while a stent 10 (e.g., a braided stent) having more than one filament 20 may require more than one weld joint 60. In some embodiments, variation(s) in sizing of the stent 10 may determine how many filaments 20 and/or how many weld joints 60 form the stent 10. In some embodiments, the stent 10 may include one weld joint 60, two weld joints 60, four weld joints 60, eight weld joints 60, ten weld joints 60, twelve weld joints 60, sixteen weld joints 60, or another suitable number of weld joints 60 generally corresponding to the number of filaments 20 that form the stent 10. In some embodiments, each weld joint 60 may define a longitudinal weld joint length. In some embodiments, a weld joint 60 may comprise only a single weld along the longitudinal weld joint length. In some embodiments, a weld joint 60 may comprise a plurality of individual welds along the longitudinal weld joint length. Other configurations, including modifications and/or combinations thereof, are also contemplated. In some embodiments, the weld joint(s) may be formed more easily and/or completely as a result of the arrangement of the flat surfaces and/or the flattened portions. For example, in some embodiments, alignment and/or abutment of the flat surfaces and/or the flattened portions may promote more even heating, melting, and/or comingling of material(s) within the weld joint and/or the weld melt pool formed when making the weld joint. In some embodiments, alignment and/or abutment of the flat surfaces and/or the flattened portions may form a smoother and/or more complete weld joint free of holes and/or voids within the weld joint, for example, when the weld melt pool cools and/or solidifies.

The materials that can be used for the various components of the stent 10 and the various elements thereof disclosed herein may include those commonly associated with medical devices. For simplicity purposes, the following discussion makes reference to the stent 10 and/or the one or more filaments 20. However, this is not intended to limit the devices and methods described herein, as the discussion may be applied to other elements, members, components, or devices disclosed herein.

In some embodiments, the stent 10 and/or the one or more filaments 20, and/or components thereof, may be made from a metallic material, a metallic alloy, a non-metallic material such as a polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys;

cobalt-chromium-molybdenum alloys (e.g., UNS: R30003 such as ELGILOY®, PHYNOX®, and the like); platinum enriched stainless steel; titanium; niobium; platinum; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the stent 10 and/or the one or more filaments 20, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the stent 10 and/or the one or more filaments 20. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stent 10 and/or the one or more filaments 20 to achieve the same result.

In some embodiments, a degree of Magnetic Resonance Imaging (MRI) compatibility is imparted into the stent 10 and/or the one or more filaments 20. For example, the stent 10 and/or the one or more filaments 20, and/or components or portions thereof, may be made of a material that does not substantially distort the image and create substantial artifacts (i.e., gaps in the image). Certain ferromagnetic materials, for example, may not be suitable because they may create artifacts in an MRI image. The stent 10 and/or the one or more filaments 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable non-metallic materials and/or polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of manufacturing a stent, comprising:
    interweaving one or more filaments around a stent mandrel, the one or more filaments each including a cross-sectional profile having at least one flattened portion, wherein the one or more filaments each include a generally round cross-sectional profile modified to form the at least one flattened portion; and
    positioning a flattened portion of a first filament portion of the one or more filaments facing a flattened portion of a second filament portion of the one or more filaments.

2. The method of claim 1, further including the step of:
    welding the flattened portion of the first filament portion of the one or more filaments to the flattened portion of the second filament portion of the one or more filaments.

3. The method of claim 2, wherein the step of welding includes at least partially melting the flattened portion of the first filament portion of the one or more filaments and the flattened portion of the second filament portion of the one or more filaments to form a weld joint therebetween.

4. The method of claim 1, wherein positioning the flattened portion of the first filament portion of the one or more filaments facing the flattened portion of the second filament portion of the one or more filaments includes vibrating the stent mandrel to orient the flattened portion of the first filament portion of the one or more filaments facing the flattened portion of the second filament portion of the one or more filaments.

5. The method of claim 1, wherein the at least one flattened portion is ground into the generally round cross-sectional profile.

6. The method of claim 1, wherein the at least one flattened portion is rolled into the generally round cross-sectional profile.

7. The method of claim 1, wherein the cross-sectional profile defines a perimeter and each flattened portion extends around less than half of the perimeter.

8. The method of claim 1, wherein the interweaving step includes forming a plurality of crossing points, each of the plurality of crossing points being formed by an upper filament portion of the one or more filaments crossing over a lower filament portion of the one or more filaments.

9. The method of claim 8, wherein a flattened portion of the lower filament portion faces a flattened portion of the upper filament portion at each of the plurality of crossing points.

10. A method of manufacturing a stent, comprising:
    interweaving one or more filaments, each including a cross-sectional profile having at least one flattened portion, around a stent mandrel such that a plurality of crossing points are formed, wherein the one or more filaments each include a generally round cross-sectional profile modified to form the at least one flattened portion, each of the plurality of crossing points being formed by a lower filament portion and an upper filament portion;
    orienting a flattened portion of the lower filament portion to face a flattened portion of the upper filament portion at each of the plurality of crossing points; and
    applying heat energy to a first filament portion of the one or more filaments and a second filament portion of the one or more filaments, the first filament portion having a flattened portion facing a flattened portion of the second filament portion, to form a weld joint between the first filament portion and the second filament portion.

11. The method of claim 10, wherein orienting the flattened portion of the lower filament portion to face the flattened portion of the upper filament portion at each of the plurality of crossing points includes vibrating the stent mandrel.

12. The method of claim 10, wherein orienting the flattened portion of the lower filament portion to face the flattened portion of the upper filament portion at each of the plurality of crossing points includes reversibly actuating the stent between a generally elongated configuration and a generally shortened configuration.

13. The method of claim 10, wherein applying heat energy includes focusing a laser beam on the first filament portion and the second filament portion.

14. The method of claim 10, wherein the flattened portion of the first filament portion abuts the flattened portion of the second filament portion.

15. A method of manufacturing a stent, comprising:
    interweaving one or more filaments around a stent mandrel, the one or more filaments each including a cross-sectional profile having at least one flattened portion, wherein the cross-sectional profile defines a perimeter and each flattened portion extends around less than half of the perimeter; and
    positioning a flattened portion of a first filament portion of the one or more filaments facing a flattened portion of a second filament portion of the one or more filaments.

16. The method of claim 15, further including the step of:
    welding the flattened portion of the first filament portion of the one or more filaments to the flattened portion of the second filament portion of the one or more filaments.

17. The method of claim 16, wherein the step of welding includes at least partially melting the flattened portion of the first filament portion of the one or more filaments and the flattened portion of the second filament portion of the one or more filaments to form a weld joint therebetween.

18. The method of claim 15, wherein the interweaving step includes forming a plurality of crossing points, each of the plurality of crossing points being formed by an upper filament portion of the one or more filaments crossing over a lower filament portion of the one or more filaments.

19. The method of claim 18, wherein a flattened portion of the lower filament portion faces a flattened portion of the upper filament portion at each of the plurality of crossing points.

* * * * *